United States Patent [19]

Matsuda et al.

[11] Patent Number: 4,806,614

[45] Date of Patent: Feb. 21, 1989

[54] SURGICAL ADHESIVE

[75] Inventors: Takehisa Matsuda, Minoo; Hiroo Iwata, Suita; Tetsuo Itoh, Shiga, all of Japan

[73] Assignee: Sanyo Chemical Industries, Ltd., Kyoto, Japan

[21] Appl. No.: 124,259

[22] Filed: Nov. 23, 1987

Related U.S. Application Data

[62] Division of Ser. No. 898,710, Aug. 21, 1986, Pat. No. 4,740,534.

[30] Foreign Application Priority Data

Aug. 30, 1985 [JP] Japan ................................ 61-192366
Aug. 30, 1985 [JP] Japan ................................ 60-192367
Jun. 9, 1986 [JP] Japan ................................ 60-134696

[51] Int. Cl.$^4$ ............................................. C08G 75/00
[52] U.S. Cl. ................................. 528/59; 128/334 R; 128/335.5; 604/307

[58] Field of Search ..................... 128/334 R, 335.5; 604/307; 528/59

[56] References Cited

U.S. PATENT DOCUMENTS 4,057,535 8/1977 Lipatova et al. .................. 260/77.5

*Primary Examiner*—Maurice J. Welsh
*Attorney, Agent, or Firm*—Oblon, Fisher, Spivak, McClelland & Maier

[57] ABSTRACT

Elastomeric or flexible surgical adhesives, comprising [A] NCO-terminated hydrophilic urethane prepolymer derived from hydrophilic polyether polyol of higher oxyethylene content, or combination of [A] with [B] unsaturated cyano compound containing cyano group attached to a carbon atom constituting the polymerizable double bond, are used for bonding of tissues, with rapid cure rate and sufficient bonding power.

23 Claims, No Drawings

SURGICAL ADHESIVE

This is a division of application Ser. No. 898,710 filed Aug. 21, 1986 now U.S. Pat. No. 4,740,534.

BACKGROUND OF THE INVENTION

It is known that urethane prepolymer from polyester glycol is used as surgical adhesive (Prog. neurol. Surg., Vol. 3, pp. 116-168, Karger, Baseland Yearn Book, Chicago 1969).

Such prepolymer, however, has drawbacks that, due to its very slow and ununiform curing characteristics, poor adhesive strength has been often found, as applied in vascular graft, resulting in massive bleeding.

SUMMARY OF THE INVENTION

It is an object of the present invention to provide a rapidly curable surgical adhesive.

It is another object of this invention to provide an surgical adhesive having high improved bonding power for tissues.

It is still another object of the invention to provide surgical bonding means with improved elasticity or flexibility.

It is yet another object of the invention to provide adhesive for surgery of lower toxicity.

Briefly, these and other objects of the present invention as hereinafter will become more readily apparent have been attained broadly by a surgical adhesive, which comprises [A] NCO-terminated hydrophilic urethane prepolymer derived from hydrophilic polyether polyol of higher oxyethylene content, or combination of [A] with [B] unsaturated cyano compound containing cyano group attached to a carbon atom constituting the polymerizable double bond.

DETAILED DESCRIPTION OF THE PREFERRED EMBODIMENTS

Said NCO-terminated hydrophilic urethane prepolymer [A], used in the surgical adhesive according to the invention, can be derived from at least one organic polyisocyanate (a) and at least one hydrophilic polyether polyol (b) with or without one or more other polyols (c).

Illustrative of suitable hydrophilic polyether polyols (b) are adducts of ethylene oxide [hereinafter referred to as EO] or combinations thereof with other alkylene oxide(s) [hereinafter referred to as AO] to one or more compounds containing at least two active hydrogen atoms, such as polyhydric alcohols, polyhydric phenols, amines, polycarboxylic acids, phosphorous acids and the like. Suitable examples of polyhydric alcohols include dihydric alcohols, such as ethylene glycol, propylene glycol, 1,3- and 1,4-butane diols, 1,6-hexane diol, neopentyl glycol, diethylene glycol, bis(hydroxymethyl)cyclohexane, bis(hydroxyethyl)benzene, hydrogenated bisphenol A, hydrogenated bisphenol F, polytetramethylene glycols, polyester diols and silanol-terminated polysiloxanes; trihydric alcohols, such as glycerol, trimethylol propane, trimethylol ethane, 1,2,3-butane triol, 1,2,6-hexane triol and polyester triols; and polyhydric alcohols having 4-8 or more hydroxyl groups, such as pentaerythritol, diglycerol, alpha-methylglucoside, sorbitol, xylitol, mannitol, glucose, fructose, sucrose, and the like. Exemplary of suitable polyhydric phenols are mono- and poly-nuclear phenols, such as hydroquinone, catechol, resorcin, pyrogallol, and bisphenols [bisphenol A, bisphenol F, bisphenol S and the like], as well as phenol-formaldehyde condensation products.

Suitable amines are inclusive of ammonia; alkanol amines, such as mono-, di- and tri-ethanol amines, isopropanol amines and the like; aliphatic, aromatic, araliphatic and alicyclic monoamines, such as $C_1$-$C_{20}$ alkyl amines [methyl, ethyl, isopropyl, butyl, octyl and lauryl amines, and the like], aniline, toluidine, naphthyl amines, benzyl amine, cyclohexyl amine and the like, aliphatic, aromatic, araliphatic and alicyclic polyamines, such as $C_2$-$C_6$ alkylene diamines [ethylene diamines], diethylene triamine, tolylenediamines, phenylenediamines, xylylenediamines, methylenedianilines, diphenyletherdiamines, isophoronediamine, cyclohexylenediamines, dicyclohexylmethanediamines and the like; and heterocyclic polyamines, such as piperazine, N-aminoethyl-piperazine, and other heterocyclic polyamines, written in Japan Patent Publication No. 21044/1980.

Suitable AO, which may be employed in combination with EO for producing polyether polyols, include, for example, propylene oxide [hereinafter referred to as PO], 1,2- 2,3-, 1,3- and 1,4-butylene oxides, styrene oxide, epichlorohydrin and the like, as well as combinations of two or more of them. Among these, preferred are PO.

Addition of EO or combination thereof with AO to active hydrogen atom-containing compounds can be carried out in the usual way, with or without catalysts [such as alkaline catalysts, amine catalysts and acidic catalysts], under normal or an elevated pressure, in a single step or multi-stages. Addition of EO and AO may be performed by random-addition, block-addition or combination of them [for instance random-addition followed by block-addition]. Preferred is random-addition.

Hydrophilic polyether polyols have equivalent weight (molecular weight per hydroxyl group) of usually 100-5,000, preferably 200-3,000, and oxyethylene content of usually at least 30%, preferably 50-90% by weight. Polyether polyols having equivalent weight higher than 5,000 are too viscous to be used as surgical adhesives; while equivalent weight less than 100 results in lack of flexibility required for surgical adhesives. Polyether polyols of oxyethylene content less than 30% by weight, having insufficient hydrophilic nature, have poor reactivity with body fluids resulting in reduced cure rate and poor bonding power with water-rich tissue. Content of the primary hydroxyl groups of polyether polyols is preferably at least 30%, more preferably at least 50%, most preferably at least 70%.

Other polyols (c), optionally used in conjunction with hydrophilic polyether polyols, include low molecular weight polyols and/or hydrophobic polyols. Examples of such polyols are polyhydric alcohols mentioned above [as raw materials for hydrophilic polyether polyols]; AO adducts (such as PO adducts) of these polyhydric alcohols or other active hydrogen atom-containing compounds; and polyester polyols. Illustrative examples of polyester polyols are condensation products of dihydric and/or trihydric alcohols [ethylene glycol, propylene glycol, 1,3- and 1,4-butane diols, 1,6-hexane diol, neopentyl glycol, diethylene glycol, glycerol, trimethylolpropane and the like] and/or polyether polyols [such as those described above] with dicarboxylic acids [aliphatic or aromatic dicarboxylic acids, such as glutaric, adipic, sebacic, fumaric, maleic, phthalic and terephthalic acids] or ester-forming derivatives thereof [anhydrides and lower alkyl esters, such as maleic and phthalic anhydrides, dimethyl terephtharate, and the like]; ring-opening polymerization products of lactones [such as epsilon-caprolactone]. Among these polyols, polyether polyols are preferred to polyester polyols.

These polyols [(b) and optionally (c)], used for producing NCO-terminated urethane prepolymer, have equivalent weight (average) of usually 100–5,000, preferably 200–3,000 and usually 2–8 hydroxyl groups, preferably 2–4 hydroxyl groups.

Suitable polyisocyanates, used in producing NCO-terminated hydrophilic urethane prepolymer [A] according to the invention, include, for example, aromatic polyisocyanates containing 6–20 carbon atoms [except carbon atoms in NCO groups], such as o-, m- and p-phenylene diisocyanates [hereinafter referred to as PDI], 2,4- and 2,6-tolylenediisocyanates [TDI], diphenylmethane-2,4'- and 4,4'-diisocyanates [MDI], naphthalene-1,5-diisocyanate, triphenylmethane-4,4',4''-triisocyanate, polymethylenepolyphenylenepolyisocyanates [PAPI] obtained by phosgenation of aniline-formaldehyde condensation products, m- and p-isocyanato-phenyl sulfonyl isocyanate, and the like; aliphatic polyisocyanates containing 2–18 carbon atoms, such as ethylenediisocyanate, tetramethylenediisocyanate, hexamethylenediisocyanate, dodecamethylenediisocyanate, 1,6,11-undecanediisocyanate, 2,2,4-trimethylhexanediisocyanate, lysine diisocyanate, 2,6-diisocyanatomethyl caproate, bis(2-isocyanato-ethyl fumarate, bis(2-iso-cyanatoethyl) carbonate, 2-isocyanato-ethyl-2,6-diiso-cyanatohexanoate, and the like; alicyclic polyisocyanates containing 4–15 carbon atoms, such as isophorone diisocyanate, dicyclohexylmethane diisocyan-ates, cyclohexylene diisocyanates, methylcyclohexylene diisocyanates, bis(2-isocyanato-ethyl) 4-cyclohexene-1,2-dicarboxylate, and the like; araliphatic polyisocyanates containing 8–15 carbon atoms, such as xylylene diisocyanates, diethylbenzene diisocyanates, and the like; and modified polyisocyanates of these polyisocyanates, containing urethane, carbodiimide, allophanate, urea, biuret, urethdione, urethimine, isocyanurate and/or oxazolidone groups, such as urethane-modified TDI, carbodiimide-modified MDI, urethane-modified MDI, and the like; as well as mixtures of two or more of them.

Among these polyisocyanates, preferred are aromatic polyisocyanates (preferably diisocyanates), particularly PDI, TDI [including 2,4- and 2,6-isomers, mixtures of them and crude TDI], MDI [including 4,4'- and 2,4'-isomers, mixtures of them and crude MDI or PAPI], and modified polyisocyanates containing urethane, carbodiimide, allophanate, urea, biuret and/or isocyanurate groups, derived from PDI, TDI and/or MDI.

The most preferred is p-PDI [hereinafter referred to as PPDI], with respect to low toxicity. Combinations of PPDI with a minor amount (usually up to 50% by weight, preferably up to 30% by weight) of one or more other polyisocyanates, as mentioned above. Among said other polyisocyanates, used in conjunction with PPDI, are aromatic polyisocyanates, particularly TDI and MDI [including crude ones and modified ones] and mixtures of them. It is preferred to react said other polyisocyanates at early stages of prepolymer production so as to provide PPDI terminated prepolymers.

In reacting at least one polyisocyanate (a) with at least one hydrophilic polyether polyol (b) and optionally one or more other polyols (c) to form NCO-terminated hydrophlic urethane prepolymers, ratio of NCO/OH is generally 1.5–5.0, preferably 1.7–3.0. The reaction of (a) with (b) and optionally (c) forming prepolymers can be performed in the usual manner. The reaction may be carried out in the presence of a catalyst. Prepolymers may be prepared by reacting (a) with a mixture of (b) and (c), or reacting successively in any order with (b) and (c). Prepolymers may be prepared by blending a prepolymer from (b) with a prepolymer from (c) [for instance, blending with a prepolymer from a low molecular weight polyol (equivalent weight 50–500) to reduce viscosity].

NCO-contents of NCO-terminated hydrophilic prepolymers are usually 1–10%, preferably 2–8% by weight. Prepolymers of NCO-content less than 1% by weight are of poor reactivity and bring about reduction of cure rate and insufficient bonding power to tissues. Higher NCO-content than 10% by weight results in brittle cured resins of poor flexibility which are not deformable following the movement of living organism.

Illustrative examples of suitable unsaturated cyano compound [B] containing cyano group attached to a carbon atom constituting the polymerizable double bond are cyano(meth)acrylic acids [cyanoacrylic acid and cyanomethacrylic acid; similar expressions are used hereinafter]; cyano(meth)acrylic esters, such as methyl cyano(meth)acrylates, ethyl cyano(meth)acrylates, isobutyl cyano(meth)acrylates and the like; (meth)acrylonitriles, cyano(meth)acrylonitriles, and the like; and mixtures of two or more of these compounds. Among these, preferred are cyanoacrylic esters, especially methyl cyanoacrylate, ethyl cyanoacrylate and iso-butyl cyanoacrylate.

In adhesive compositions comprising said hydrophilic urethane prepolymer [A] and said unsaturated cyano compound [B], content of [A] is usually 20–90%, preferably 30–70%, based on the total weight of [A] and [B]. Use of less than 20% of [A] results in poor flexibility and poor bonding ability with living organism. Combination of [A] with 10% or more of [B] provide more rapid cure rate, which can be applied for bonding of blood vessels, wherein quick-curing is required. By varying the ratio of [A] to [B], there can be attained desired hardness in accordance with movement of living organism. Adhesives containing higher amount of [A] are effective for applications requiring flexibility, such as bonding of blood vessels; while adhesives of lower content of [A], providing relatively higher rigidity, are suitable for bonding of bone or circumference thereof.

Adhesives of this invention may contain, if necessary, fillers [for example, carbon black, metal oxides, such as red iron oxide and titanium dioxide, silicates, such as calcium silicates and sodium silicates, acrylic resin powders, various ceramic powders, and the like]; softening agents [such as DBP(dibutylphosphate), DOP(dioctylphosphate), TCP(tricresylphosphate), tributoxyethylphosphates, and other esters of various types]; stabilizers, such as trimethyldihydroquinone, phenylbetanaphthyl amine, p-isopropoxydiphenylamine, diphenyl-p-phenylene diamine, and the like. These additives may be used in an amounts of usually 0–20%, preferably 0–5%, based on the weight of the adhesive according to the invention.

Both said NCO-terminated prepolymer(s) and said cyano compound(s) can being about rapid polymerization in the presence of trace amounts of water such as moisture in air and result in forming tough membrane. Accordingly, it is necessary to use dehydrated ones as these main components and also other compounding additives, and it is preferred to shut off air during production of adhesives. Adhesives, thus obtained, can be stored for a long period of time within airtight vessels, such as ampule.

In applying adhesives of the present invention in surgery, application methods include those by using brushes, tweezers, applicators, specially-designed spatula or syringes, or the like; and those by spray coating using innert gases, such as Freons, nitrogen or the like. Bonding of tissues can be achieved, for example, by direct coating techniques, simply applying the adhesive to the tissues; by cover-coating techniques, using, as an aid for hemostasis or anastomosis, thin sheets or meshes made of polyesters (such as Dacron), oxidized cellulose, collagen, polyurethanes or the like, cotton-like materials, or fragments of tissues, such as veins, musculation or mascular membrane or the like [wherein these materials are applied onto the affected parts followed by coating thereon the adhesives]; or by sealing techniques for sutured parts, wherein sutures are partly applied followed by applying the adhesive to seal the remaining conjugation parts. The adhesives of the invention can be used, not only for tissure adhesion, but also as coating, embolus or sealing materials in cardiovascular surgery via direct coating or injection by catheters. Applicable tissues include, for example, blood vessels, heart, lung, esophagus, stomach, skin and the like.

Having generally described the invention, a more complete understanding can be obtained by reference to certain specific examples, which are included for purposes of illustration only and are not intended to be limiting unless otherwise specified.

Raw materials used in the following examples are as follows:
PEO: Polyethyleneoxide,
PPO: Polypropyleneoxide,
PEG: polyetheleneglycol,
PPG: Polypropyleneglycol,
PTMG: Polytetramethyleneglycol,
ECA: Ethyl cyanoacrylate,
MCA: Methyl cyanoacrylate,
BCA: Iso-butyl cyanoacrylate.

Preparation of Prepolymers

NCO-terminated prepolymers A1 to A4, B1 to B4 and I to III were prepared by mixing each polyether polyol, dehydrated under reduced pressure, with each polyisocyanate and reacting them for 8 hours at 80 C.

Prepolymer A1
A polyether polyol [a PEO/PPO random copolymer having an average M.W. of 3,000 and oxyethylene content of 80%] was reacted with PPDI to obtain a NCO-terminated hydrophilic urethane prepolymer having an NCO-content of 2.5%.

Prepolymer A2
A polyether polyol [a PEO/PPO random copolymer having an average M.W. of 4,000 and oxyethylene content of 60%] was reacted with PPDI to obtain a NCO-terminated hydrophilic urethane prepolymer having an NCO-content of 3.5%.

Prepolymer A3
A polyether polyol [a mixture of 80 parts of a PEG having an average M.W. of 2,000 and 20 parts of polypropyleneglycol having an average M.W. of 200] was reacted with PPDI to obtain a NCO-terminated hydrophilic urethane prepolymer having an NCO-content of 6.4%.

Prepolymer A4
A polyether polyol [a PTMG-PEO block copolymer having an average M.W. of 2,000 and oxyethylene content of 50%] was reacted with PPDI to obtain a NCO-terminated hydrophilic urethane prepolymer having an NCO-content of 6.7%.

Prepolymer B1
A polyether polyol [a PEO/PPO random copolymer having an average M.W. of 3,000 and oxyethylene content of 80%] was reacted with TDI to obtain a NCO-terminated hydrophilic urethane prepolymer having an NCO-content of 2.5%.

Prepolymer B2
A polyether polyol [a PEO/PPO random copolymer having an average M.W. of 4,000 and oxyethylene content of 60%] was reacted with MDI to obtain a NCO-terminated hydrophilic urethane prepolymer having an NCO-content of 3.5%.

Prepolymer B3
A polyether polyol [a mixture of 80 parts of a PEG having an average M.W. of 2,000 and 20 parts of polypropyleneglycol having an average M.W. of 200] was reacted with TDI to obtain a NCO-terminated hydrophilic urethane prepolymer having an NCO-content of 6.4%.

Prepolymer B4
A polyether polyol [a PTMG-PEO block copolymer having an average M.W. of 2,000 and oxyethylene content of 50%] was reacted with TDI to obtain a NCO-terminated hydrophilic urethane prepolymer having an NCO-content of 6.7%.

Prepolymer I
A polyether polyol [a PTMG having an average M.W. of 1,000] was reacted with TDI to obtain a NCO-terminated hydrophobic urethane prepolymer having an NCO-content of 6.7%.

Prepolymer II
A polyether polyol [a PEO/PPO random copolymer having an average M.W. of 3,000 and oxyethylene content of 20%] was reacted with TDI to obtain a NCO-terminated hydrophobic urethane prepolymer having an NCO-content of 2.5%.

Prepolymer III
A polyether polyol [a PEO/PPO random copolymer having an average M.W. of 3,000 and oxyethylene content of 10%] was reacted with TDI to obtain a NCO-terminated hydrophobic urethane prepolymer having an NCO-content of 2.5%.

Preparation of Surgical Adhesives

Surgical adhesives as follows were prepared.

Examples 1 to 4

Surgical adhesives consisting essentially of Prepolymers A1, A2, A3 and A4, respectively.

Example 5

A surgical adhesive, obtained by mixing and dehydrating 50 parts of Prepolymer A1 with 50 parts of ECA.

Examples 6 to 10

Surgical adhesives, obtained by substituting Prepolymers B1, B2, B3 and B4 for Prepolymers A1, A2, A3 and A4, respectively.

Example 11

A surgical adhesive, obtained by mixing and dehydrating 70 parts of Prepolymer B2 with 30 parts of MCA.

Example 12

A surgical adhesive, obtained by mixing and dehydrating 50 parts of Prepolymer B3 with 50 parts of BCA.

Example 13

A surgical adhesive, obtained by mixing and dehydrating 40 parts of Prepolymer B4 with 60 parts of ECA.

Comparative Example 1

A surgical adhesive consisting essentially of ECA.

Comparative Examples 2 and 3

Surgical adhesive consisting essentially of Prepolymers I and II, respectively.

Comparative Example 4

A surgical adhesive, obtained by dissolving 7 parts of a nitrile rubber (nitrile content: 38–40%) into 50 parts of dehydrated dry nitromethane, followed by adding thereto under stirring 7 parts of ECA and 1 part of TDI.

Comparative Example 5

A surgical adhesive, obtained by mixing and dehydrating 50 parts of Prepolymer III with 50 parts of ECA.

Testing of Surgical Adhesives

Carotid artery of goat, heparinized in order to avoid effects of blood coagulation, was clamped at about 5 cm of distance and then incised 3 mm along with the longitudinal direction, followed by coating a small amount of each adhesive. Within several minutes after application of the adhesive, the clamps were removed. Then, the tissue adhesivity and hemostasis were carefully evaluated.

The results were as shown in Table 1.

TABLE 1

| Surgical Adhesive | | Cure Time (sec.) | Flexibility | Bonding Power | Clinical sign at adhesive joints |
|---|---|---|---|---|---|
| Example | 1 | 25 | O | O | Very good adhesivity. No bleeding after declamping. |
| | 2 | 24 | O | O | Very good adhesivity. No bleeding after declamping. |
| | 3 | 20 | O | O | Very good adhesivity. No bleeding after declamping. |
| | 4 | 35 | O | O | Very good adhesivity. No bleeding after declamping. |
| | 5 | 7 | O | O | Very good adhesivity. No bleeding after declamping. |
| Example | 6 | 35 | O | O | Very good adhesivity. No bleeding after declamping. |
| | 7 | 36 | O | O | Very good adhesivity. No bleeding after declamping. |
| | 8 | 29 | O | O | Very good adhesivity. No bleeding after declamping. |
| | 9 | 42 | O | O | Very good adhesivity. No bleeding after declamping. |
| | 10 | 10 | O | O | Very good adhesivity. No bleeding after declamping. |
| | 11 | 15 | O | O | Very good adhesivity. No bleeding after declamping. |
| | 12 | 9 | O | O | Very good adhesivity. No bleeding after declamping. |
| | 13 | 10 | O | O | Very good adhesivity. No bleeding after declamping. |
| Comparative Example | 1 | 5 | X | X | Very fast curing. Delamination immediately after declamping. Massive bleeding. |
| | 2 | ≧400 | O | X | Slow and inhomogeneous curing characteristics. Bleeding from adhesive joints |
| | 3 | 400 | O | X | Very slow curing. Due to premature curing, bleeding after declamping. |
| | 4 | 350 | O | Δ | Very slow curing. Premature curing. Bleeding. |
| | 5 | 400 | O | X | Very slow curing. Inhomogeneous curing. Bleeding from adhesive joints |

What is claimed as new and desired to be secured by Letters Patent is:

1. A method for surgical bonding of tissue, which comprises applying thereto a surgical adhesive consisting essentially of at least one NCO-terminated hydrophilic urethane prepolymer, derived from at least one organic polyisocyanate and a polyol component comprising at least one hydrophilic polyether polyol having an oxyethylene content of at least 30%.

2. The method of claim 1, wherein said prepolymer has an isocyanate-content of 1–10% by weight.

3. The method of claim 1, wherein said polyol component has an oxyethylene content of at least 30%.

4. The method of claim 1, wherein said polyol component has an equivalent weight (average) of 100–5,000 and a functionality (average) of 2–8.

5. The method of claim 1, wherein said polyisocyanate is at least one selected from the group consisting of aromatic polyisocyanates containing 6–20 carbon atoms, aliphatic polyisocyanates containing 2–18 carbon atoms, alicyclic polyisocyanates containing 4–15 carbon atoms, araliphatic polyisocyanates containing 8–15 carbon atoms, except carbon atoms in NCO groups, and modified polyisocyanates of these polyisocyanates containing one or more of urethane, carbodiimide, allophanate, urea, biuret, urethdione, urethimine, isocyanurate and oxazolidone groups.

6. The method of claim 1, wherein said polyisocyanate is p-phenylene diisocyanate, or a combination thereof with one or more other polyisocyanates.

7. The method of claim 1, wherein said hydrophilic polyether polyol is at least one adduct of ethylene oxide or a combination thereof with one or more other alkylene oxides to at least one compound containing two or more active hydrogen atoms.

8. The method of claim 7, wherein said compound containing two or more active hydrogen atoms is at least one selected from the group consisting of polyhydric alcohols, polyhydric phenols, amines, polycarboxylic acids and phosphorous acids.

9. The method of claim 1, wherein said hydrophilic polyether polyol is at least one selected from the group consisting of polyoxyethylene polyols, polyoxyethylene/oxypropylene polyols and polyoxyethylene/oxybutylene polyols.

10. The method of claim 1, wherein said polyol component comprises said hydrophilic polyether polyol and at least one other polyol selected from the group consisting of low molecular weight polyols, hydrophobic polyether polyols and polyester polyols.

11. The method of claim 1, wherein said prepolymer is obtained by reacting said polyisocyanate with said polyol component in such an amount providing NCO-/OH ratio of 1.5–5.0.

12. A method for surgical bonding of tissue, which comprises applying thereto a surgical adhesive comprising
(A) at least one NCO-terminated hydrophilic urethane prepolymer, derived from at least one organic polyisocyanate and a polyol component comprising at least one hydrophilic polyether polyol having an oxyethylene content of at least 30%, and
(B) at least one unsaturated cyano compound containing a cyano group attached to a carbon atom constituting the polymerizable double bond.

13. The method of claim 12, which comprises 20–90% by weight of said cyano compound.

14. The method of claim 12, wherein said cyano compound is at least one compound selected from the group consisting of cyanoacrylic acid, cyanomethacrylic acid, cyanoacrylates, cyanomethacrylates, acrylonitrile, methacrylonitrile, cyanoacrylonitrile and cyanomethacrylonitrile.

15. The method of claim 12, wherein said cyano compound is at least one cyanoacrylic ester selected from the group consisting of methyl cyanoacrylate, ethyl cyanoacrylate and iso-butyl cyanoacrylate.

16. The method of claim 1, which contains up to 20% by weight of at least one additive selected from the group consisting of carbon black, metal oxides, silicates, acrylic resin powders, ceramic powders, softening agents, and stabilizers.

17. The method of claim 12, which contains up to 20% by weight of at least one additive selected from the group consisting of carbon black, metal oxides, silicates, acrylic resin powders, ceramic powders, softening agents, and stabilizers.

18. The method of claim 1, wherein said tissue is blood vessel, heart, lung, esophagus, stomach or skin.

19. The method of claim 12, wherein said tissue is blood vessel, heart, lung, esophagus, stomach or skin.

20. The method of claim 1, wherein the surgical adhesive is substantially free from any phenolic compound.

21. The method of claim 1, wherein said hydrophilic polyether polyol is at least one adduct of a combination of ethylene oxide with one or more other alkylene oxides to at least one compound containing two or more active hydrogen atoms.

22. The method of claim 1, wherein said hydrophilic polyether polyol is at least one member selected from the group consisting of polyoxyethylene/oxypropylene polyols and polyoxyethylene/oxybutylene polyols.

23. The method of claim 1, wherein the polyol component has an oxyethylene content of at most 90%.

* * * * *